United States Patent [19]

Römer

[11] Patent Number: 4,515,802

[45] Date of Patent: May 7, 1985

[54] ANALGESIC PREPARATIONS

[75] Inventor: Dietmar Römer, Allschwil, Switzerland

[73] Assignee: Sandoz Ltd., Basle, Switzerland

[21] Appl. No.: 587,571

[22] Filed: Mar. 8, 1984

[30] Foreign Application Priority Data

Mar. 9, 1983 [GB] United Kingdom ................. 8306473

[51] Int. Cl.³ .................... A61K 31/48; A61K 31/165; A61K 31/415; A61K 31/475
[52] U.S. Cl. ..................................... 514/288; 514/367
[58] Field of Search ............................ 424/273 R, 324

[56] References Cited

U.S. PATENT DOCUMENTS 4,442,084 4/1984 Römer .................................. 424/251

OTHER PUBLICATIONS

Sayers et al., Drug/Res. 30(1), No. 5, (1980), pp. 793–803.
Lepisto, P., Therapeutic Research, vol. 30, No. 2, (1981), pp. 141–146.
Chem. Abst.-98, (1983), 40582w.

Primary Examiner—Stanley J. Friedman
Attorney, Agent, or Firm—Gerald D. Sharkin; Robert S. Honor; Walter F. Jewell

[57] ABSTRACT

A process for the production of an improved and well tolerated analgesic preparation of paracetamol which comprises formulating tizanidine and paracetamol using e.g. granulating techniques and optionally putting up into tablet form, e.g. using compression and moulding techniques to produce tablets and suppositories.

15 Claims, No Drawings

ANALGESIC PREPARATIONS

The present invention relates to analgesic preparations.

The relief of pain, especially acute pain, is a well-recognized medical need.

An ideal pain-killing analgesic preparation should be one which is effective in relieving a wide variety of pains in different parts of the body for a wide variety of subjects, yet is sufficiently safe to be used without medical supervision by the general public, and is unlikely to be consciously taken in sufficiently large overdoses to be fatal. New analgesic agents have been developed but very few have entered the market due to a variety of reasons, e.g. CNS side effects, liver toxicity or too narrow a therapeutic range. Many fixed combinations based on aspirin and/or paracetamol in combination with other active agents have been proposed.

Paracetamol is a very widely used analgesic agent. However, it may cause some undesirable side effects, in particular in very high doses acute hepatotoxicity may be observed.

Tizanidine, also known as 5-chloro-4-(2-imidazolin-2-yl-amino)-2,1,3-benzothiazole, is an effective, rapidly-acting myotonolytic agent. It is preferably used in the form of the hydrochloride (All weights hereinafter refer to the amount of base unless otherwise specified). The pharmacological activity of tizanidine has been published, e.g. in A. C. Sayers et al., Arzneim.-Forschung, 30, Nr.5, p. 793–803 (1980) and Triangle, Vol. 20, No. 4, 1981, p. 151. Tizanidine has not yet been introduced in any country. However reports of clinical trials have appeared in the literature.

According to the invention administration of a fixed combination of tizanidine and paracetamol may exhibit particularly advantageous and unforeseen properties, e.g. it may provide excellent analgesic and muscle relaxant activity and may be very well tolerated. For example very little gastric irritation may be observed unlike with anti-inflammatories. Moreover, fixed combinations of tizanidine and paracetamol may be made in unit dose forms which are effective analgesic preparations for a large number of subjects, and which may be safer to use in practice than paracetamol alone.

As indicated above tizanidine has been administered as a myotonolytic agent, e.g. for the treatment of muscle spasms and in some clinical trials paracetamol may have been administered separately as an analgesic, e.g. for the treatment of severe pain associated with the muscle spasms.

The amounts of the paracetamol administered will of course have varied widely from patient to patient. Whereas the regimen of tizanidine administration was generally regular, e.g. one capsule three times a day, the paracetamol was usually administered as an analgesic on an irregular basis, whenever the need arose and in varying amounts depending on the need, and not necessarily at the same time as the tizanidine. Clearly fixed combinations of tizanidine and paracetamol had never been contemplated before and the simple treatment of pain especially pain other than that associated with muscle spasms using such a fixed combination had not been contemplated.

The administration of a fixed combination of tizanidine and paracetamol is accordingly indicated as being of particular advantage as e.g. minor analgesics in inducing analgesia, e.g. for the treatment of pain.

In one aspect the present invention therefore provides a pharmaceutical preparation comprising tizanidine and paracetamol.

Moreover it is especially advantageous for the treatment of migraine to have dihydro-ergotamine also present.

The analgesic effect and tolerance of the fixed combination according to the invention may be observed in standard pharmacological tests and in clinical trials.

One pharmacological test is the adjuvans arthritis pain test on the rat [A. W. Pircio et al., Europ.J.of Pharmacology 31, 207–215 (1975)], effected as follows:

Male rats (OFA strain) weighing 110–120 g were injected subcutaneously with 0.1 ml of a Mycobacterum butyricum suspension in paraffin oil (0.6 mg mycobact./0.1 ml oil) into the root of the tail. The effects of the test treatment were investigated 18 days later when a marked arthritis in the hindpaws had developed. Thirty minutes before administration the foot joint of the right or the left hindpaw was flexed by means of a Statham transducer until vocalisation occurred. Rats that did not vocalise were discarded from the test. One, 3 and 5 hours after oral administration of the test substances, the flexion procedure was repeated. The administered pressure was expressed in arbitrary units. The threshold was expressed as the average value of three successive measurements. Those animals in which the threshold was doubled were considered to be protected. The $ED_{50}$ (95% confidence limits), estimated for each post-treatment time according to the method described by Litchfield and Wilcoxon (Litchfield, J. T. et al., J. Pharm. exp. Ther. 96, 99, 1949), was taken as the dose that produced protection in 50% of the animals.

Tizanidine is administered p.o. at doses from 0.1 to 3 mg/kg and paracetamol at doses from 10 to 100 mg/kg p.o. separately or in combination. Dihydroergotamine may be administered at a dosage of from 0.1 to 3 mg/kg p.o.

One clinical trial pattern is a controlled, double-blind single-dose parallel group comparison of a fixed combination according to the invention, e.g. containing 2 mg tizanidine and 250 mg or 325 mg paracetamol, optionally containing 0.5 mg of dihydro-ergotamine, 2 doses of paracetamol (each dose 250 mg or 325 mg), 1 dose of tizanidine (1 or 2 mg) and placebo.

The groups each comprise about 30 subjects aged from 20 to 65 years, suffering from (a) moderate or severe pain due to extraction of compacted molars or other procedures involving bone surgery
(b) moderate or severe pain due to episiotomy
(c) moderate or severe pain due to other surgical operations
(d) moderate or severe pain due to tension headaches, and
(e) moderate or severe pain due to vascular headaches, including migraine.

The subjects had not receive any analgesic within 4 hours of the administration and had not eaten within 1 hour before or after administration. The trial is effected over 3 to 6 hours during which time no additional analgesics, sedatives or tranquillizers or other psychotropic drugs are administered. The medication is given with water. The pain intensity and relief is evaluated on the basis of a scoring system at the time of administration and every hour after administration. Side effects as well as intensity thereof are also recorded. For example levels in the blood of enzymes indicative of liver toxicity.

In the above tests the fixed combination of the invention may show surprisingly effective analgesic activity and may be very well tolerated, side-effects incidence being low and distributed.

The preparations according to the invention may be prepared in conventional manner using conventional galenical techniques. For example compositions may be prepared by working together tizanidine and paracetamol into a fixed pharmaceutical composition, optionally in administration with other conventional pharmaceutical excipients such as fillers, granulating agents, disintegrating agents, binding agents, lubricating agents, dispersing agents, wetting agents, stabilising agents and dyestuffs.

The preparations of the invention are preferably put up in solid form, e.g. as tablets, powder, granules, suppositories and capsules. Preferably they are put up in unit dosage form particularly in solid unit dosage form in the form of a suppository or especially a tablet. Such forms may contain tizanidine and paracetamol separately, e.g. in separate layers in a layer or mantle tablet.

Accordingly, in a further aspect the present invention provides a process for the production of a pharmaceutical preparation which comprises formulating tizanidine and paracetamol and optionally putting up the formulation into unit dosage form.

The administration of a fixed combination of tizanidine and paracetamol is therefore useful in inducing analgesia, e.g. in the treatment of painful conditions such as post-operative pain, post-traumatic pain, e.g. after dental surgery, headache, e.g. tension headache, vascular headache, migraine, and musculo-skeletal pain, especially that associated with muscle spasms resulting from degenerative disease of the spine and other joints.

The exact daily dosage of tizanidine and paracetamol for use in the method of the invention will of course depend upon, inter alia, the mode of administration and the severity of the pain to be treated.

A suitable indicated daily dosage of tizanidine is in the range of from about 6 to about 16 mg.

Conveniently the active agents are administered in sustained release form or alternatively in divided doses 2 to 4 times a day containing e.g. from about 2 to about 4 mg of tizanidine for oral administration.

An indicated weight ratio of tizanidine to paracetamol is from about 1:50 to about 1:500 or 1:300, e.g. from 1:100 to 1:250 and preferably from 1:100 to 1:200. Examples of ratios are 1:500 and preferably 1:125, and 2:325, 1.:250.

Examples of preferred amounts of tizanidine in unit dosage forms are 1 and 2 mg of tizanidine.

Examples of preferred amounts of paracetamol in unit dosage forms are 250, 325 and 500 mg of paracetamol.

For example a unit dosage form may contain from about 2 to 4 mg tizanidine and from about 200 to 500 mg paracetamol, e.g. 2 mg tizanidine and 200 to 300 or 200 to 400 mg paracetamol.

If desired dihydroergotamine, preferably in the form of the mesylate may be present. A typical daily dose is from 2 to 8 mg. Typically from about 0.5 to 4 mg e.g. 0.5 to 1.5 mg of dihydroergotamine is present in unit dosage form of the invention.

The following Examples are illustrative of compositions for use in the invention.

(Primojel is a disintegrating agent based on sodium starch glycolate available from AVEBE Veendam Holland).

EXAMPLE 1

Tablet suitable for oral administration

Tablets containing the ingredient indicated below may be prepared by conventional techniques and are useful for oral administrtion once or twice a day in the treatment of pain.

| Ingredient | Weight (mg) |
| --- | --- |
| Tizanidine hydrochloride | 2.288 (= 2 mg base) |
| Paracetamol | 250.00 |
| Corn Starch | 20.00 |
| Polyvinylpyrrolidone | 12.00 |
| Cross-linked polyvinylpyrrolidone | 15.00 |
| Lactose | 88.712 |
| Magnesium stearate | 2.00 |
| | 390.00 |

If desired the tablet may be scored so that it may be easily divided into two.

EXAMPLE 2

Tablet suitable for oral administration

Tablets containing the ingredients indicated below may be prepared by conventional techniques and are useful for oral administration once or twice a day in the treatment of pain.

| Ingredient | Weight (mg) |
| --- | --- |
| Tizanidine hydrochloride | 4.576 (= 4 mg base) |
| Paracetamol | 500.00 |
| Hydroxypropylcellulose | 20.00 |
| Sodium carboxymethyl cellulose | 11.00 |
| Lactose | 24.00 |
| Microcrystalline cellulose | 52.424 |
| Magnesium stearate | 3.00 |
| | 615.00 |

If desired the tablet may be scored so that it may be easily divided into two.

EXAMPLE 3

Tablet suitable for oral administration

| Ingredient | Weight (mg) |
| --- | --- |
| Charge A: | |
| Tizanidine hydrochloride | 2.288 (= 2 mg base) |
| Hydroxypropylcellulose | 2.00 |
| Lactose | 51.712 |
| Primojel R | 6.00 |
| Charge B: | |
| Paracetamol | 250.00 |
| Lactose (200 mesh) | 50.00 |
| Corn Starch | 2.00 |
| Charge C | |
| Corn Starch | 5.00 |
| Primojel R | 5.00 |
| Magnesium stearate | 1.00 |
| | 375.0 mg |

Charge A and B are thoroughly mixed by conventional techniques and compounded, again by conventional mixing, with charge C. The combined composition A+B+C is pressed into tablet forms of 11 mm diameter suitable for oral administration once or twice daily in the treatment of pain.

EXAMPLE 4

Tablet suitable for oral administration

| Ingredient | Weight (mg) |
|---|---|
| Charge A | |
| Tizanidine hydrochloride | 2.288 (= 2 mg base) |
| Hydroxypropylcellulose | 1.1 |
| Primojel R | 5.712 |
| Charge B: | |
| Paracetamol | 250.00 |
| Microcrystalline cellulose (e.g. Avicel R PH 102) | 53.00 |
| Lactose | 13.00 |
| Charge C: | |
| Primojel R | 18.00 |
| Magnesium stearate | 0.90 |
| | 344.00 mg |

Charges A and B are thoroughly mixed by conventional techniques and compounded, again by conventional mixing, with charge C. The combined composition A+B+C is pressed into tablet forms suitable for oral administration once or twice daily in the treatment of pain.

EXAMPLE 5

Suppositories

Suppositories may be formulated in conventional manner containing for example:

| | Weight (mg) | Weight (mg) |
|---|---|---|
| Tizanidine hydrochloride | 2.288 | 4.576 |
| Paracetamol | 250 | 500 |
| Massa ad suppositora, e.g. semi-synthetic glycerides such as Suppocire AM or Witepsol H-15 | 1747.712 | 1495.424 |
| | 2000 | 2000 |

If desired ca. 1.7 mg of the Massa ad suppositora may be replaced by 1.7 mg dihydroergotamine mesylate.

EXAMPLE 6

Capsules

| | Composition per capsule | |
|---|---|---|
| | Weight | |
| Ingredient | mg | mg |
| (A) Tizanidine hydrochloride | 1.144 | 2.288 |
| (B) Excipient Mixture (see below) | 14.106 | 22.962 |
| (C) Paracetamol granulate (see below) | 334.75 | 334.75 |
| (D) Excipient mixture (see below) | 100.00 | 90.00 |
| | 450 | 450 |

| Excipient Mixture = | Lactose (200 mesh) | 58.5% |
|---|---|---|
| | Corn Starch | 40% |
| | Colloidal silica | 0.5% |
| | Magnesium stearate | 1% |
| Paracetamol granulate = | Paracetamol | 97.1% |
| | Corn Starch | 2.9% |

MANUFACTURE

Ingredients (A) and (B) are mixed together. In another vessel ingredients (C) and (D) are mixed together. The two mixtures are then combined and encapsulated.

If desired 0.6 mg of the excipient mixture may be replaced by the same amount of dihydroergotamine mesylate.

What we claim is:

1. A pharmaceutical preparation comprising tizanidine and paracetamol wherein the weight ratio of tizanidine to paracetamol is from about 1:50 to about 1:500.

2. A preparation according to claim 1 in the form of a suppository.

3. A preparation according to claim 1 in unit dosage form for oral administration.

4. A preparation according to claim 1 in the form of a tablet.

5. A preparation according to claim 1 comprising 1 mg tizanidine.

6. A preparation according to claim 1 comprising 2 mg tizanidine.

7. A preparation according to claim 1 comprising 2 to 4 mg tizanidine.

8. A preparation according to claim 1 comprising 200 to 500 mg paracetamol.

9. A preparation according to claim 1 wherein the tizanidine:paracetamol weight ratio is from 1:100 to 1:300.

10. A preparation according to claim 1 comprising 1 mg tizanidine and 250 mg paracetamol.

11. A preparation according to claim 1 comprising 2 mg tizanidine and 325 mg paracetamol.

12. A preparation according to claim 1 comprising 2 mg tizanidine and 500 mg paracetamol.

13. A preparation according to claim 1 comprising 2 mg tizanidine and 250 mg paracetamol.

14. A preparation according to claim 1 containing also dihydroergotamine.

15. A preparation according to claim 14 containing from 0.5 to 4 mg dihydroergotamine.

* * * * *